US006816599B2

(12) United States Patent
Thiede et al.

(10) Patent No.: US 6,816,599 B2
(45) Date of Patent: Nov. 9, 2004

(54) EAR LEVEL DEVICE FOR SYNTHESIZING MUSIC

(75) Inventors: Thilo Volker Thiede, Gentofte (DK); Carl Ludvigsen, Valby (DK)

(73) Assignee: Topholm & Westermann APS, Vaerlose (DK)

(*) Notice: Subject to any disclaimer, the term of this patent is extended or adjusted under 35 U.S.C. 154(b) by 161 days.

(21) Appl. No.: 09/725,233

(22) Filed: Nov. 29, 2000

(65) Prior Publication Data

US 2002/0090100 A1 Jul. 11, 2002

Related U.S. Application Data

(63) Continuation-in-part of application No. 09/717,018, filed on Nov. 22, 2000, now abandoned.

(30) Foreign Application Priority Data

Nov. 14, 2000 (EP) .............................................. 00610115

(51) Int. Cl.$^7$ .............................................. H04R 25/00
(52) U.S. Cl. ....................... 381/314; 381/73.1; 381/315
(58) Field of Search .................................. 381/312, 313, 381/314, 317, 320, 328, 330, 23.1, 73.1; 600/559; 181/129, 130, 135

(56) References Cited

U.S. PATENT DOCUMENTS

| 3,570,473 | A |   | 3/1971 | Konvalin |
| 4,735,968 | A |   | 4/1988 | Guth |
| 4,759,070 | A |   | 7/1988 | Voroba et al. |
| 4,915,001 | A |   | 4/1990 | Dillard |
| 5,325,872 | A |   | 7/1994 | Westermann |
| 5,357,048 | A |   | 10/1994 | Sgroi |
| 5,403,262 | A |   | 4/1995 | Gooch |
| 5,405,153 | A |   | 4/1995 | Hauck |
| 5,832,431 | A |   | 11/1998 | Severson et al. |
| 6,047,074 | A |   | 4/2000 | Zoels et al. |
| 6,198,971 | B1 | * | 3/2001 | Leysieffer .................... 607/55 |

FOREIGN PATENT DOCUMENTS

| DE | 4427216 A1 | 2/1996 |
| SE | 8105983-4 | 7/1983 |
| WO | WO 94/09606 | 4/1994 |

OTHER PUBLICATIONS

Lars Kindermann, "MusiNum—The Music in the Numbers", Oct. 25, 2000—Internet site http://www.forwiss.uni-erlangen.de/~kinderma/musinum/musinum.html.

Larry Solomon, "The Fractal Nature of Music", Oct. 25, 2000—Internet site http://www.community,pima.edu/users/larry/fracmus.htm.

* cited by examiner

*Primary Examiner*—Curtis Kuntz
*Assistant Examiner*—Brian Ensey
(74) *Attorney, Agent, or Firm*—Sughrue Mion, PLLC

(57) ABSTRACT

The present invention relates to an ear level electronic device comprising a housing that is adapted to be worn behind the ear, in the ear, or in the ear canal, and to enclose a music synthesizer for generation of an electrical signal representing music and an output transducer for conversion of the electrical signal into sound. In the device, sound generators are controlled by pseudo-random number generators generating sequences of self-similar numbers whereby music is synthesized that is surprisingly relaxing and comfortable to listen to. Further, a music sequence generated by such a number generator is extremely long so that a person listening to the music does not have a perception of being listening to repeated music sequences.

37 Claims, 6 Drawing Sheets

EAR LEVEL DEVICE FOR SYNTHESIZING MUSIC

This is a Continuation-in-Part of application Ser. No. 09/717,018 filed Nov. 22, 2000, now abandoned.

FIELD OF THE INVENTION

The present invention relates to an ear level electronic device comprising a housing that is adapted to be worn behind the ear, in the ear, or in the ear canal, and to enclose a music synthesizer for generation of an electrical signal representing music and an output transducer for conversion of the electrical signal into sound.

BACKGROUND OF THE INVENTION

Music is a sequence of sounds, such as tones, chords, etc, preferably generated in pleasant patterns. In the present context, the term music denotes a sequence of sounds that has a duration allowing a listener to listen comfortably to the music for extended periods of time. Preferably, music is a sequence of sounds with a duration that is longer than 5 seconds, preferably longer than 10 seconds, more preferred longer than 20 seconds, even more preferred longer than 30 seconds, still more preferred longer than one minute, and most preferred substantially longer than one minute.

The electronic device may relieve living beings of stress and anxiety, and in particular living beings may be relieved of stress, anxiety and upsets caused by tinnitus when listening to music synthesized by the device.

Tinnitus occurs in a subjective and an objective form. A person that has a sensation of head noises, such as buzzing, ringing, whistling, hissing, etc, is said to suffer from tinnitus. When the person has the sensation without an external cause, the tinnitus is subjective. When the head noises can be heard or measured by an examiner, the tinnitus is objective. The head noises may be heard intermittently or the noises may vary over time in another way.

It is well-known that a person suffering from tinnitus may perceive a relief from tinnitus by listening to an externally generated sound.

An externally generated sound may mask tinnitus. In general, the term masking refers to the influence on tinnitus during presence of another sound. However, the influence may continue after termination of the masking sound. The masking may be complete meaning that tinnitus is not heard during presence of the masking sound or, the masking may be partial meaning that tinnitus is heard with reduced loudness during presence of the masking sound. Masking devices generating sounds based on electronic noise signals are well-known in the art. Noise generators, e.g. pseudo-random noise generators, are employed providing stationary noise with a certain bandwidth. However, typically, random noise is not comfortable to listen to, and a positive masking effect requires that the noise is more pleasant to listen to than the tinnitus itself.

It is also known that externally generated sounds may inhibit tinnitus so that the tinnitus is not heard (complete inhibition) or is heard with reduced loudness (partial inhibition) after termination of the inhibiting sound. Typically, the tinnitus is heard again seconds or minutes after termination of the inhibiting sound but sometimes the tinnitus is inhibited for hours or days. Pure tones or noise with a narrow bandwidth have been shown to inhibit tinnitus. E.g. in U.S. Pat. No. 5,325,872, a device is disclosed for inhibiting tinnitus with pure tones by repetitively sweeping the tone across a narrow frequency interval around the frequency of the tinnitus. The repetition period may be selected between 0.1 and 1000 s.

Through habituation, a person's perception of tinnitus may be changed by exposure of the person to sound during a longer period of time. Typically, other therapeutic methods are also included in the treatment of the person. By habituation, the tinnitus perception is changed so that nuisance caused by tinnitus is eliminated or reduced. Typically, noise signals are used for habituation. The loudness of the noise signals is adjusted so that the tinnitus is still heard. This is important for habituation to be obtained. Thus, a complete masking is not allowed.

However, it is a disadvantage of utilization of noise signals, such as white or pink noise signals, that the corresponding sounds typically cause some nuisance to the listener and may mask signals of interest to the listener.

Finally, it is known that listening to sounds in general may relieve nuisance caused by tinnitus. Listening to music may for example have a positive effect on a person's perception of tinnitus. Further, music may also affect emotions caused by tinnitus, such as stress, by having a general relaxing effect whereby the positive effect of listening is increased. This treatment is known as desensibilisation. DE-A1-44 27 216 discloses a device generating music of a specific category selected by the tinnitus patient, e.g. classic, pop or meditation music. The music sequence may be stored magnetically on a tape or be stored in digitized form in a semiconductor memory. It is suggested that the music signals may be transmitted to a hearing aid by wireless transmission means.

Tinnitus may occur together with another hearing impairment. In WO-A-94/09606, a tinnitus masking device is disclosed for masking tinnitus where the frequency of the tinnitus occurs in a narrow frequency band in which the hearing is impaired. Thus, this device also stimulates the sensory nerves in a narrow frequency band around the frequency of the tinnitus.

SUMMARY OF THE INVENTION

It is an object of the present invention to provide an apparatus for generation of a signal representing sound that is emotionally neutral and non-distracting so that a person suffering from tinnitus may listen comfortably to sounds based on this signal for extended periods of time with a sensation of relief and thus without getting distracted with the synthesized sounds.

It is a further object of the invention to provide the apparatus in a hearing aid type of apparatus, i.e. an apparatus that is worn behind the ear, or in the ear, or in the ear canal as is well-known in the art of hearing aids.

Preferably, the apparatus is used for desensibilisation or for habituation.

The device may incorporate means for turning the music synthesizer off manually or automatically. The device may further comprise means for detecting a desired signal, such as speech, music, etc, and for turning the music synthesizer off automatically upon detection of the desired signal.

Further, the synthesized sounds should not mask any signals of interest, e.g. communication signals and other signals that the person needs or desires to hear.

According to a first aspect of the present invention an ear level electronic device is provided, comprising a housing that is adapted to be worn behind the ear, in the ear, or in the ear canal, and to enclose a music synthesizer for generation of a first electrical signal representing music and an output transducer for conversion of the first electrical signal into sound.

An ear level electronic device is a device that is worn like a hearing aid, i.e. behind the ear, in the ear, or in the ear canal, and wherein the output of the output transducer is led to the eardrum in a way that is well-known in the art of hearing aids.

The device may be incorporated into a hearing aid, such as a digital hearing aid that comprises an input transducer, the output transducer, a digital signal processing means, and the music synthesizer for generating the electronic signal representing music to be reproduced by the output transducer. Preferably, the music synthesizer is incorporated in the digital signal processing means, i.e. the digital signal processing means is adapted to perform the functions of the music synthesizer.

The music synthesizer may be adapted to generate the synthesized music at the output transducer with a loudness or amplitude level that does not mask the tinnitus completely, i.e. the user may still perceive to hear the tinnitus sound at a reduced level.

The music synthesizer may comprise a sound generator and preferably, the synthesizer comprises a set of sound generators. The sound generators may be controlled digitally.

Each sound generator may be adapted to generate an electronic signal representing a tone of a specific loudness and frequency and with a specific spectral content, thus, representing a tone with a specific sonorous figure. Further, fade-in and fade-out time constants of a generated tone may be controlled. The adjustable parameters, such as loudness, frequency, spectral content, fade-in, fade-out and tone duration, of the sound generators may be controlled digitally by a controller included in the music synthesizer.

The controller may comprise one or more pseudo-random number generators for generation of sequences of pseudo-random numbers. One or more parameters of a sound generator may be determined based on the value of a number generated by one of the one or more pseudo-random number generators. Different number generators may generate different sequences of pseudo-random numbers controlling different parameters of a selected sound generator.

In a pseudo-random number sequence, the next number can not be determined from the previous number or a short sequence of the previous numbers if the initial conditions of the number sequence are not known.

The controller may further comprise a temporal generator comprising a pseudo-random generator for determination of time periods between start of generation of successive tones.

At least one of the pseudo-random number generators may be adapted to generate a sequence of self-similar numbers, or a sequence of fractal numbers, preferably a sequence of self-similar numbers.

According to a second aspect of the present invention a tinnitus treatment method is provided, comprising the steps of synthesizing music with a music synthesizer for automatic generation of an electronic signal representing music, converting the signal into sound, and directing the sound towards an ear of a person suffering from tinnitus.

The method may further comprise the step of compensating for another hearing deficiency of the person.

The method may further comprise the step of adjusting the sound loudness to a loudness level that do not to mask the tinnitus completely.

The method may also incorporate the steps of a method of synthesizing music provided according to a third aspect of the present invention, the method comprising the steps of generating a random number with a pseudo-random number generator, and calculating parameters of a tone from the generated random number.

A sound generator may be used to generate the tone with the calculated parameters. Various parameters, such as amplitude, frequency, spectral content, fade-in, fade-out and tone duration, etc, of a generated tone may be determined based on the generated number. Different parameters may be determined from numbers occurring in different sequences of pseudo-random number sequences. Further, a period between the start of succeeding tones may be determined from a number in a sequence of pseudo-random numbers, preferably a different sequence of pseudo-random numbers. The pseudo-random number sequence may be a sequence of self-similar numbers, or a sequence of fractal numbers, preferably a sequence of self-similar numbers.

It is an important advantage of the present invention that synthesizing music with pseudo-random number generators eliminates a need for a large memory capable of storing a selection of recorded music sufficiently large for the user not to be upset with repeated listening to the same music. For example, carrying a separate device with larger capacity and thus a broader selection of music, would in general be considered cumbersome and incompatible with the daily use.

It has further been shown that music synthesized utilizing a pseudo-random number generator generating self-similar numbers, or fractal numbers, etc, is surprisingly relaxing and comfortable to listen to. Further, a music sequence generated by such a number generator is extremely long so that a person listening to the music does not perceive listening to repeated music sequences. Further it has been noted that, typically, a person with tinnitus listening to the music does not experience a complete masking of the tinnitus but rather a comfortable distraction from the tinnitus whereby the person becomes capable of concentrating on other desired matters.

Thus, by synthesizing music according to the present invention, it is achieved that the synthesized music is perceived to be virtually non-repetitive, i.e. a listener does not recognize a repeated sequence. Further, although the synthesized music substantially covers the audible spectrum, it does not mask signals of interest.

It is a further advantage that the electronic device according to the present invention may be comprised in a hearing aid or in a hearing aid type of housing to be worn behind the ear, in the ear, or in the ear canal, without a need for a remote unit for storage and transmission of music to the hearing aid or the hearing aid type of housing.

According to a fourth aspect of the present invention a binaural electronic device is provided, comprising a first electronic device of the above-mentioned type to be positioned in one ear of a user, and a second electronic device of the above-mentioned type to be positioned in the other ear of the user.

According to a fifth aspect of the present invention a method of the above-mentioned type is provided, wherein music is synthesized and directed towards one ear of a user, and different music is synthesized and directed towards the other ear of the user.

It is an important advantage of the binaural electronic device that the device is capable of synthesizing different music in different ears of a user. A user with tinnitus has experienced that listening to a binaural device according to the present invention masks the tinnitus completely even when the music is generated at a very low level of loudness.

This desirable effect is believed to be caused by cognitive competition in the brain caused by listening to different music in different ears. The first and second electronic devices may produce the same music sequence displaced in time in relation to each other by an interval of at least two tones. In the present context, a person is said to listen to different music in each ear when each ear regularly does not listen to the same tones. For example, the same music sequence may be played in each ear with a specific displacement in time between the two ears. The time displacement may be adjustable by the user so that the user may perform an optimum selection of a time displacement value that provides optimum cognitive competition in the brain, i.e. reducing the perceived tinnitus effect to a minimum with a minimum of induced disturbance of the user. Alternatively, the time displacement is determined by a random difference in start-up times of each of the music synthesizers.

It is preferred that a sequence of random numbers is provided by at least one of the following methods:

selection from tabulated random numbers, synthesized by a pseudo random number generator, synthesized by a self-similar number generator, or synthesized by means of natural random events, such as 1/f-noise which is well-known to have a fractal character.

Circuitry operating according to one of these methods are easily incorporated in a hearing aid, and thus a remote unit for generation and transmission of music to the hearing aid is not required.

Sometimes, a remote, portable device may be preferred, e.g. by persons suffering from tinnitus who do not have another hearing deficiency. Such a device can be of a very small size, such as the size of a completely-in-the-canal hearing aid, and may include means for wireless communication. The remote device is carried by the user and transmits music to either one or both ears, e.g. to a wireless earphone or a wireless, preferably open, earplug. A remote device may also be utilized with a binaural system for transmission of identical or different music to each ear.

In a preferred embodiment of the invention the digital signal processing means is further adapted to provide compensation for hearing impairment. This allows the hearing aid to be used by persons suffering from tinnitus and from hearing impairment.

In such an embodiment of the present invention, the synthesized music is preferably introduced in the signal path before hearing impairment compensation so that the full frequency range of the synthesized music may be heard by the user of the hearing aid.

BRIEF DESCRIPTION OF THE DRAWINGS

Still other objects of the present invention will become apparent to those skilled in the art from the following description wherein the invention will be explained in greater detail. By way of example, there is shown and described a preferred embodiment of this invention. As will be realized, the invention is capable of other different embodiments, and its several details are capable of modification in various, obvious aspects all without departing from the invention. Accordingly, the drawings and descriptions will be regarded as illustrative in nature and not as restrictive. In the drawing.

DETAILED DESCRIPTION OF THE PREFERRED EMBODIMENTS

Figure 1:
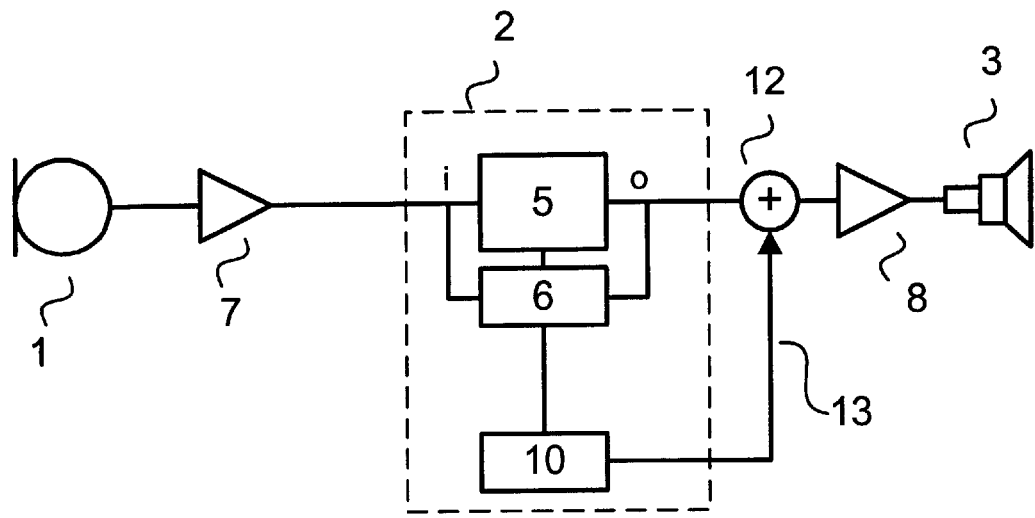
FIG. 1 is a schematic diagram of a portable electronic device according to the present invention.

FIG. 1 shows a schematic diagram of a hearing aid with an electronic device according to the invention. The hearing aid comprises a microphone 1 for reception of sound from the environment and generation of a corresponding electronic signal. The input transducer may be of a directional type, e.g. the input transducer may comprise more than one microphone, wherein several input signals are combined into a single signal. The electronic signal is fed to a digital signal processor 2 via an A/D converter 7. If appropriate, the A/D converter may be preceded by a preamplifier (not shown). If the user suffers from a hearing impairment in addition to tinnitus, the digital signal processor 2 processes the signal for correction of the hearing impairment and preferably, the synthesized music is introduced in the signal path before hearing impairment compensation so that the full frequency range of the synthesized music may be heard by the user of the hearing aid.

The hearing aid further comprises a music synthesizer 10, and the digital signal processor 2 comprises a hearing aid processor 5 and a control unit 6 for controlling the music synthesizer 10. In the present embodiment, the music synthesizer 10 is integrated in the digital signal processor 2.

Figure 2:
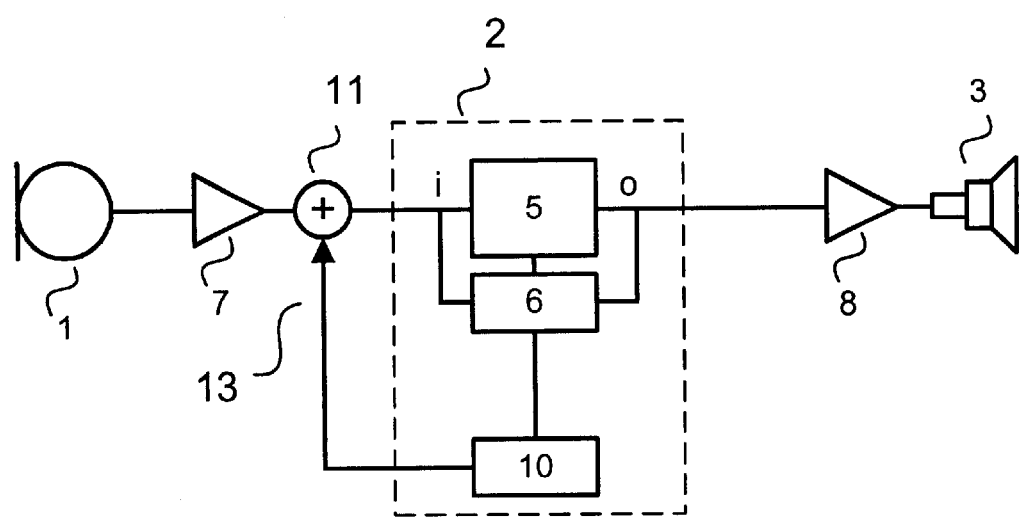
FIG. 2 is a schematic diagram of a second embodiment of the invention.

As shown in FIGS. 1 and 2, the output signal of the music synthesizer 10 may enter the main signal path of the hearing aid at a point either before or after the digital signal processor 2, at the respective summing nodes 11 or 12 via a connection 13.

Figure 3:
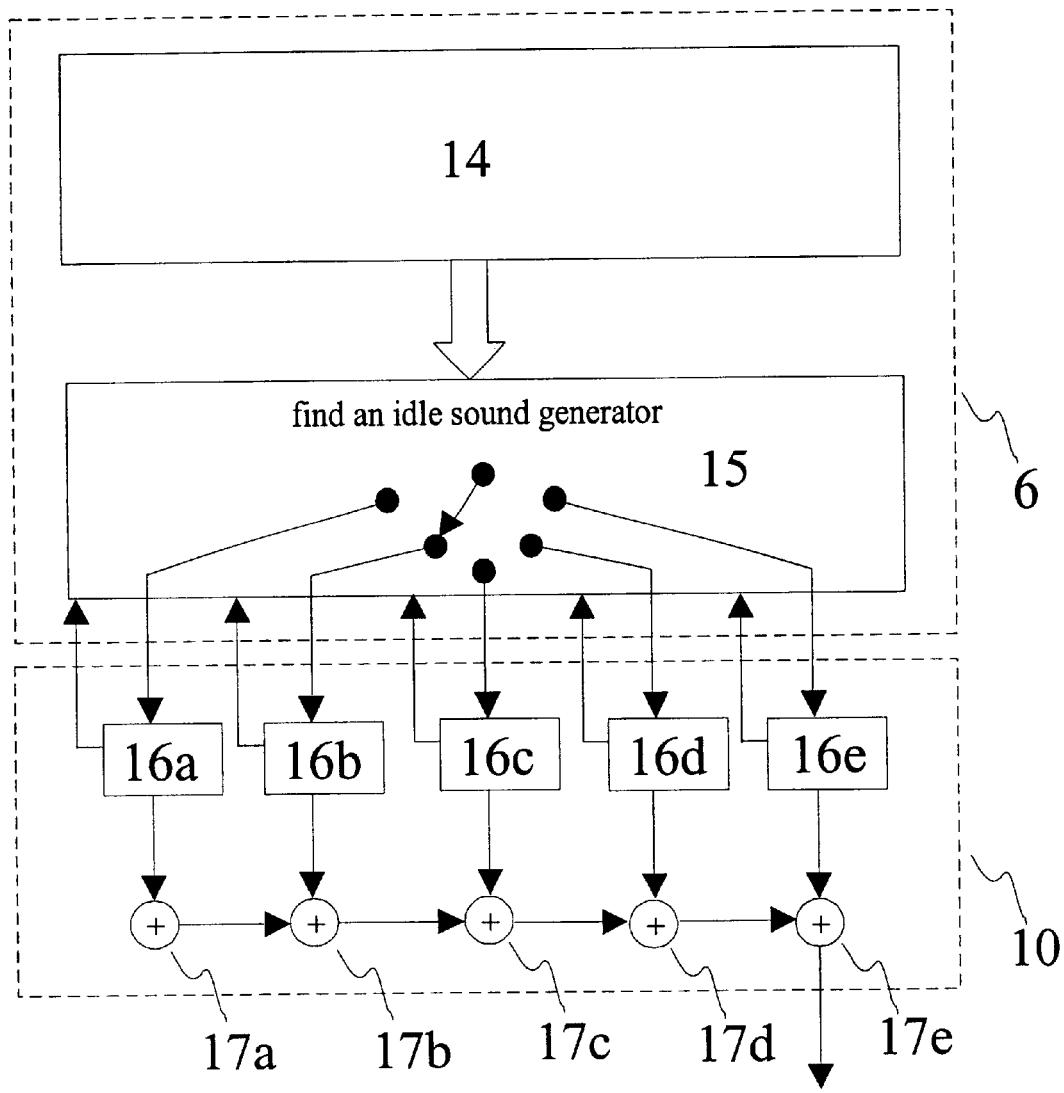
FIG. 3 is a schematic diagram of a set of sound generators.

As shown in more detail in FIG. 3, the electronic device comprises a set of sound generators 16a–16e for generation of synthesized music. A sound generator is shown in further detail in FIG. 6. Each of the sound generators comprises a damped oscillator 161 that is excited or activated by an impulse. Various parameters of the sound generator 16 that determine the waveform of the signal generated by the sound generator 16 are adjusted by the controller 6. The parameters determine frequency, maximum amplitude, duration, rise-time, fall-time, and spectral content of the generated signal. These parameters are indicated in the plot of a generated signal shown in FIG. 7. In this way, the sound generator 16 may simulate a known instrument, such as a piano, a flute, etc. Thus, upon activation, a sound generator generates a signal representing a specific tone with a specific loudness, sonorous figure and duration.

As shown in FIG. 3, the controller 6 comprises a sound generator control unit 14 and a selector unit 15 for selection of an idle sound generator from the set of sound generators 16a–16e. Preferably, the control unit 14 comprises means for adjustment of music loudness for example by setting an average amplitude of the output of each respective signal generator. This adjustment can be either automatic or user controlled or a combination thereof, e.g. the user can select a balance between loudness of music and environmental sounds, the actual music loudness being controlled automatically in accordance with the current mode of operation of the hearing aid. Alternatively, the sound level is adjusted, during a fitting procedure, to have a level compliant with the hearing threshold level (HTL) and the tinnitus level.

The outputs of the sound generators 16a–16e are added to a combined signal by adders 17a–17e and output on output line 13 for injection into the signal path of the hearing aid at an appropriate point 11, 12 by injection means, such as adders, mixers, or other signal combining units.

The controller 6, 14 controls the process of synthesizing music by controlling time of activation and the parameters of each of the sound generators. Parameters, such as harmonic content, relating to the sonorous figure of a tone remain constant from tone to tone. The values of the parameters relating to the specific tone to be generated, such as frequency, duration, amplitude, etc, for each of the sound generators are determined by mapping random numbers to values of these parameters. Thus, the controller 6 further comprises a set of pseudo-random number generators for generation of random numbers. For each sound generator to be activated, a specific pseudo-random number generator generates a number for determination of a respective specific parameter. A plurality of sound generators may be grouped together for synthesizing tones with the same sonorous figure thereby simulating an instrument that is capable of playing chords, such as a piano, a guitar, etc. A chord to be synthesized may be determined by mapping of the output of a specific pseudo-random number generator.

In the present embodiment of the invention, music is synthesized that will be perceived to be generated by three instruments. However, further variability of the synthesized music may be provided by varying the number of instruments, i.e. the number of sound generators, that is currently active synthesizing music. Thus, activation of a specific sound generator or a specific group of sound generators may be determined by mapping of the output of a specific pseudo-random number generator.

Optionally, various categories of music, such as classical music, jazz music, etc, are user selectable. For each selectable music category a set of instruments to be used for synthesizing music is predetermined. The set of instruments is defined by number of active sound generators and respective sets of parameters defining instrument types. Further, an algorithm for mapping of pseudo-random number values to respective parameter values is determined by the controller 6, 14. These predetermined selections may for example be based on a statistical analysis of the selectable categories of music. For example, a set of parameters for synthesizing Baroque music includes parameters of a harpsichord while parameters of an electric guitar are not included in such a set of parameters. Also, the number of occurrences of changes in time intervals between tone starts is reduced by using e.g. every fourth random number to control the rhythm. Likewise, a set of parameters for synthesizing so called electronic music, e.g. New Age music, includes parameters of electronic instruments, such as synthesizers, electric guitars, etc, and the synthesized music sequence has to have a large number of occurrences of extended tones. This last feature could be obtained by a re-mapping of the mapping that control tone duration.

In this way it is possible to synthesize music having an improved resemblance to the users preferred music category.

Accordingly the number of sound generators must exceed the number of instruments to be played. The illustrated embodiment has five sound generators and three instruments. However, this is an illustrative example only, and the actual number of sound generators may be greater, e.g. ten.

In the present embodiment the number of instrument voices are determined initially. Further variability may be added to the synthesized music by varying the number of active instruments, i.e. sound generators and groups of sound generators, wherein the number of active instruments is controlled by yet another pseudo-random number generator. For example, the instruments may be divided into an instrument group that remains active during synthesizing, and a solo group, the activation of which is controlled by the yet another random number generator. Alternatively, the random number could be mapped to different sub-sets of the instruments of the set of instruments that is available in the music program in question.

Figure 4:
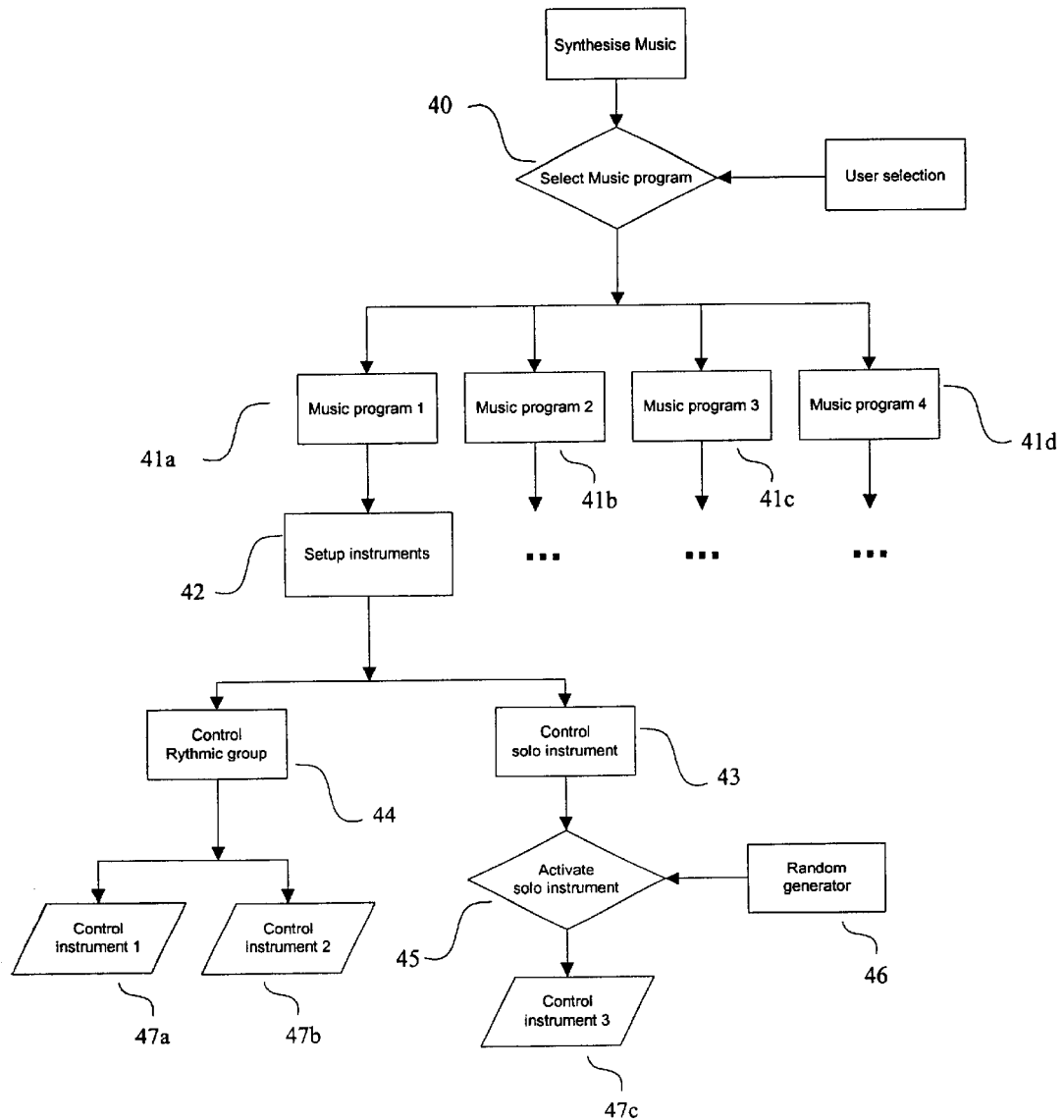
FIG. 4 is a flow chart of an algorithm for synthesizing music.

The algorithm for generation of synthesized music is shown in more detail in FIG. 4. In FIG. 4, the processing performed by the controller 6, 14 shown in FIG. 3 for controlling the sound generators is illustrated.

At block 40, the user may select a desired music category by selecting a corresponding music program 1–4. Four different programs 41a . . . 41d are shown as an example, however any desired number of music categories may be made available to the user. Upon selection of the desired music program 41a . . . 41d, the corresponding number and types of instruments are determined by the controller 6, 14.

Furthermore, parameters such as tempo, use of solo instrument, and use of extended tones are determined.

Figure 5:
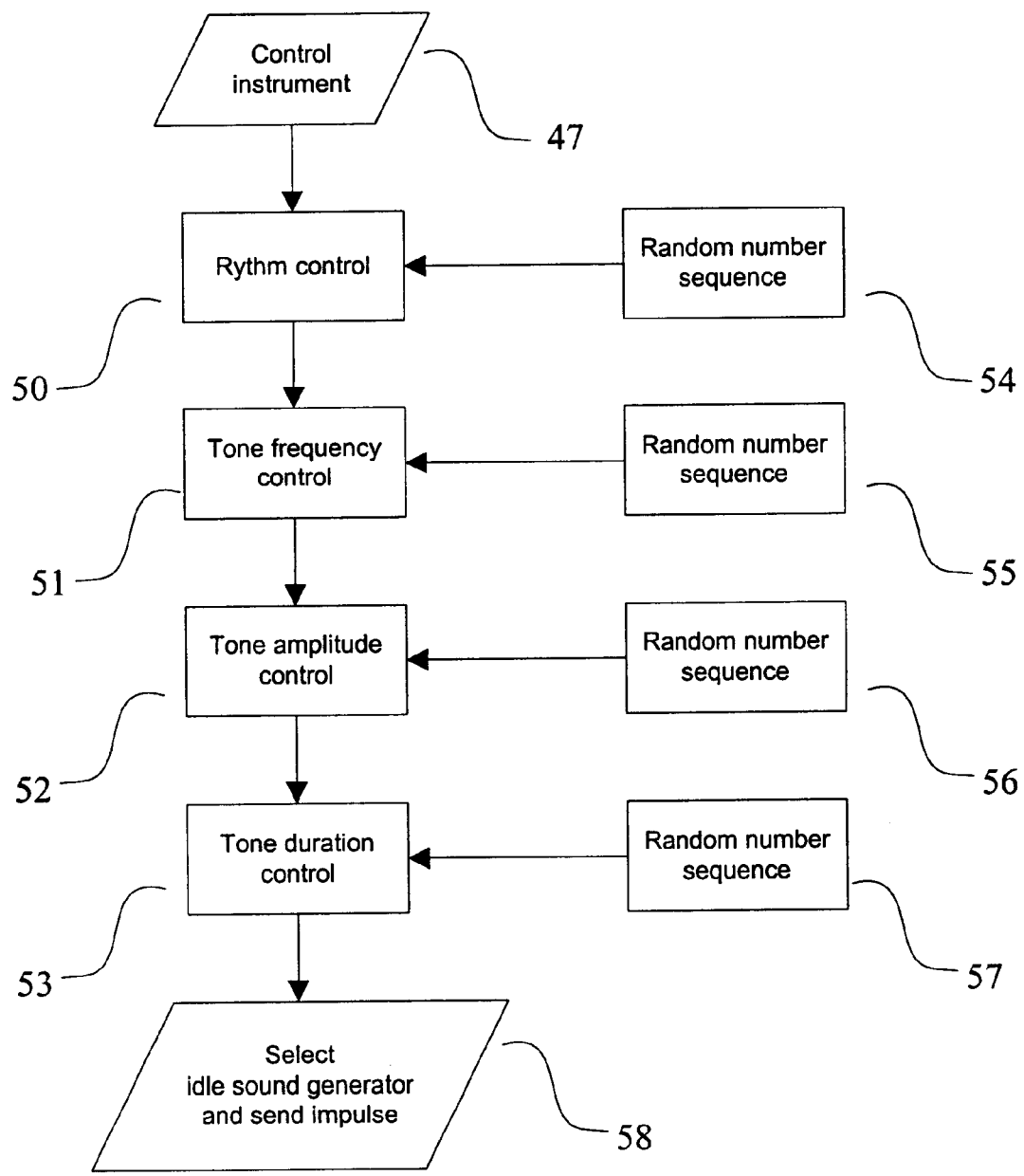
FIG. 5 is a flow chart of an algorithm for controlling a sound generator.

Having determined the parameters based on the selection of music category, i.e. music program, music synthesizing starts. Optionally, a solo instrument may be utilized at block 43 as previously described. Activation of the solo instrument is controlled at block 45 by a sequence of random numbers generated at block 46. The range of random numbers is mapped to two states of activation, either on or off so that the solo instrument is switched on or off randomly. In order to obtain a low switching rate, the rate of generation of the corresponding random numbers is kept low, e.g. corresponding to 10 bars of the synthesized music. Likewise, the duty cycle of the solo instrument is determined by proper selection of the mapping of random numbers to the activation state. At block 47a, 47b, etc, tone generation starts as described in further detail below with reference to FIG. 5.

Although a solo instrument may increase the variability of the synthesized music it may not be desired to activate the solo instrument, since it may increase the users attention to the music thereby preventing attention to other desired matters.

As indicated at block 44, music is synthesized by an instrument group that remains constant during music synthesizing. Thus, no switching feature is available for this group of instruments. Tone generation by a sound generator is further illustrated in the flow chart shown in FIG. 5. At block 50, a sequence of random numbers 54 are used to control tone start time. For this purpose, the random numbers 54 are mapped to a selection of tone intervals, e.g. ¼, ⅛, ⅜ and ¹⁄₁₆ notes. Further, it has been shown that it is desirable to control the sum of tone durations within each bar of the synthesized music to match the number of beats in a bar. As with the control of the switching of the solo instrument, it is possible to adjust the probability of tone variations by either adjusting the frequency of generation (or the read-out) of the random numbers and/or by re-mapping the tone mapping.

In addition, the amplitude, tone duration and frequency of the generated tones are controlled at blocks 52, 53 and 51, respectively, by sequences of respective random numbers 55, 56 and 57. For this purpose the random numbers are mapped to a scaling value, such that the parameter, e.g. frequency, is mapped to a range around a selected value, the selected value being a characteristic of the instrument (e.g. flute having a higher characteristic value than a cello). For example instrument frequency may denote the frequency of the lowest tone that can be played by that instrument. Again, it is possible to adjust the probability of variations by either adjusting the frequency of generation (or the read-out) of the random numbers and/or by re-mapping the tone mapping.

In the block 52 the amplitude of the tone is set by mapping the random number generated in block 56 to a relative amplitude factor or, simply using the random number as the relative amplitude factor. This factor is multiplied with the average amplitude previously set by the controller 6, 14 in order to determine the amplitude of the tone.

In the block 51 the tone frequency is set by mapping the random number generated in block 55 to a frequency factor. This factor is multiplied with the instrument frequency previously set by the controller 6, 14 in order to generate the frequency of the tone. The mapping results in generation of tones of the desired tone scale. For instruments synthesizing chords, the mapping algorithm, which is configured in block 42, may involve selection from a table of frequencies corresponding to tones of given chords.

Figure 6:
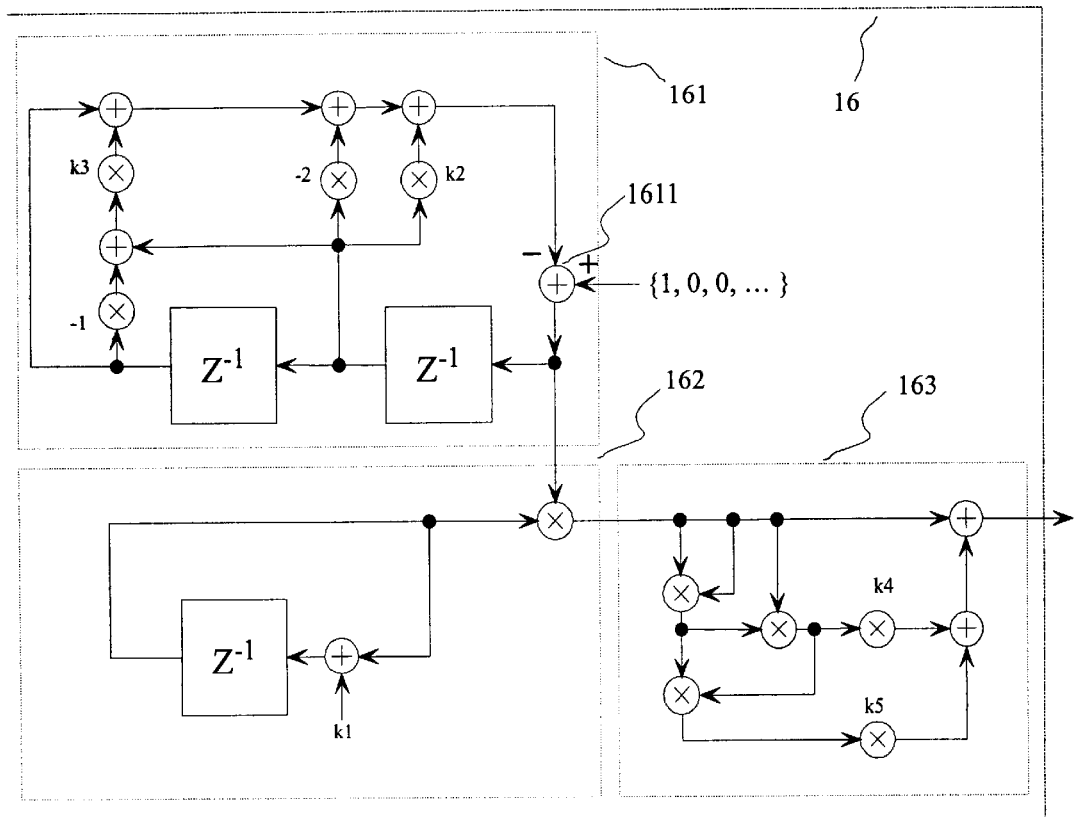
FIG. 6 is a schematic diagram of a sound generator.

At block 58, the controller 15 selects an idle sound generator, transfers the parameters, and activates the generator by transmission of an impulse to the generator (the sequence $\{1, 0, 0, \ldots\}$ as shown in FIG. 6).

It should be noted that some parameters may be determined from the output of one common pseudo-random number generator whereby the device is simplified, probably at the expense of variability of the synthesized music.

A sequence of self-similar numbers may be generated by the following algorithms:

1) Select a binary integer N1 with a predetermined number n of bits.
2) Add a second binary integer N2 to N1, N2 being either 2x−1 or 2x+1, where x<n.
3) Count the number of bits having the value '1' in the result. This number is the final result.
4) Repeat from step 2) to generate next number, iteratively using the sum of N1 and N2 as a new N1.

Other random numbers may be used to dither parameters of generated sounds, e.g. dithering frequency, duration of the tone and decay time, in order to further increase the variability of the synthesized music.

It is preferred to generate a self-similar number sequence. Self-similar numbers may be generated in various ways. A preferred way is to sum the bits of binary numbers in a binary counting sequence, i.e. 0, 1, 10, 11, 100, 101, 110, 111, 1000 etc. whereby the sequence 0, 1, 1, 2, 1, 2, 2, 3, 1 etc, is generated. It is noticed that a sequence formed by every second value of this sequence is identical to the original sequence. Likewise, a sequence that is formed by every fourth value or every $2^n$ th value is identical to the original sequence. This is a characterizing feature of self-similar number sequences and this feature is closely related to the scaling invariance of fractal number sequences. It is to be noted that self-similar numbers are a sub-class of fractal numbers since linear fractals are exactly similar on different scales (i.e. self-similar numbers) while non-linear fractals are statistically similar on different scales (cf. Larry Solomon "The fractal nature on music" on the internet at URL http://www.community.pima.edu/users/larry/fracmus.htm).

Associating these bit sums with tones according to a predetermined scheme will produce a synthesized music sequence. It is not a requirement that all the values or values at fixed intervals are selected for the use for musical notes. This is due to the scale invariance of fractal sequences which is well-known in the art of generation of synthesized music, e.g. from the internet article Kindermann, L., "MusiNum—The Music in the Numbers", available from the Internet at URL http://www.forwiss.uni-erlangen.de/~kinderma/, as of Oct. 25, 2000.

The synthesized music which may be produced e.g. by the above method, is far from simple melodic sequences such as doorbells or the like, and actually does give an impression not unlike that of actual music composed by a person.

In FIG. 6 there is depicted an embodiment of a sound generator 16. The sound generator 16 incorporates a second order IIR filter for producing an exponentially decaying sine-wave when excited with a single input impulse, as it is shown at point 1611 in the Figure. The IIR filter 161 is followed by a multiplier 162 with a linear decaying factor. The multiplier 162 causes the signal amplitude of the generated signal to reach zero within a finite time period. A signal indicating termination of tone generation is provided as indicated with feedback paths in FIG. 3 thereby indicating that the sound generator 16 is available for generating a new sound.

Further the sound generator 16 comprises a distortion circuit 163 for adding harmonics to the generated signal. Preferably, the distortion function is a fifth order polynomial where $k_4$ and $k_5$ are the third and fifth order coefficients, respectively, of the polynomial. Alternatively, there is a number of techniques available to the skilled person for production of harmonic distortion, e.g. clipping of the generated signal in combination with an adjustable equalizer. Advantageously, this distortion circuit is able to generate different harmonics characteristic of different instruments (voices) so that each sound generator may generate a signal representing the sound of any desired instrument to be utilized in the music synthesizer.

The sound generator 16 operates at a fixed sampling frequency $f_{samp}$. It uses four input parameters for generating specific sounds, the desired frequency f, the fade-out time $T_{fadeout}$, and the two distortion coefficients $k_4$ and $k_5$.

From these input parameters and the sampling frequency the factors $k_1$, $k_2$ and $k_3$ are computed from the following equations.

$$k_1 = \frac{-1}{T_{fadeout} f_{samp}}$$

$$k_2 = 4 \cdot \sin^2\left(\pi \frac{f}{f_{samp}}\right) \cong 4 \cdot \left(\left(\pi \frac{f}{f_{samp}}\right) - \frac{1}{6}\left(\pi \frac{f}{f_{samp}}\right)^3\right)^2$$

$$k_3 = \frac{2}{\tau \cdot f_{samp}}$$

where τ is the time-constant in the exponential decay.

The oscillator block 161 has a second-order z-transform of the form $$H(z) = \frac{z^2}{(1 - k_3) + z(k_2 + k_3 - 2) + z^2}$$

so that fade-in and fade-out time constants are determined by the $k_3$ coefficient.

Likewise, an exponential fade-in of the sound generator may be provided by a modified oscillator wherein the amplitude is modified by a fade-in gain factor of e.g. $(1-\exp(-t/t_r))$.

Figure 7:
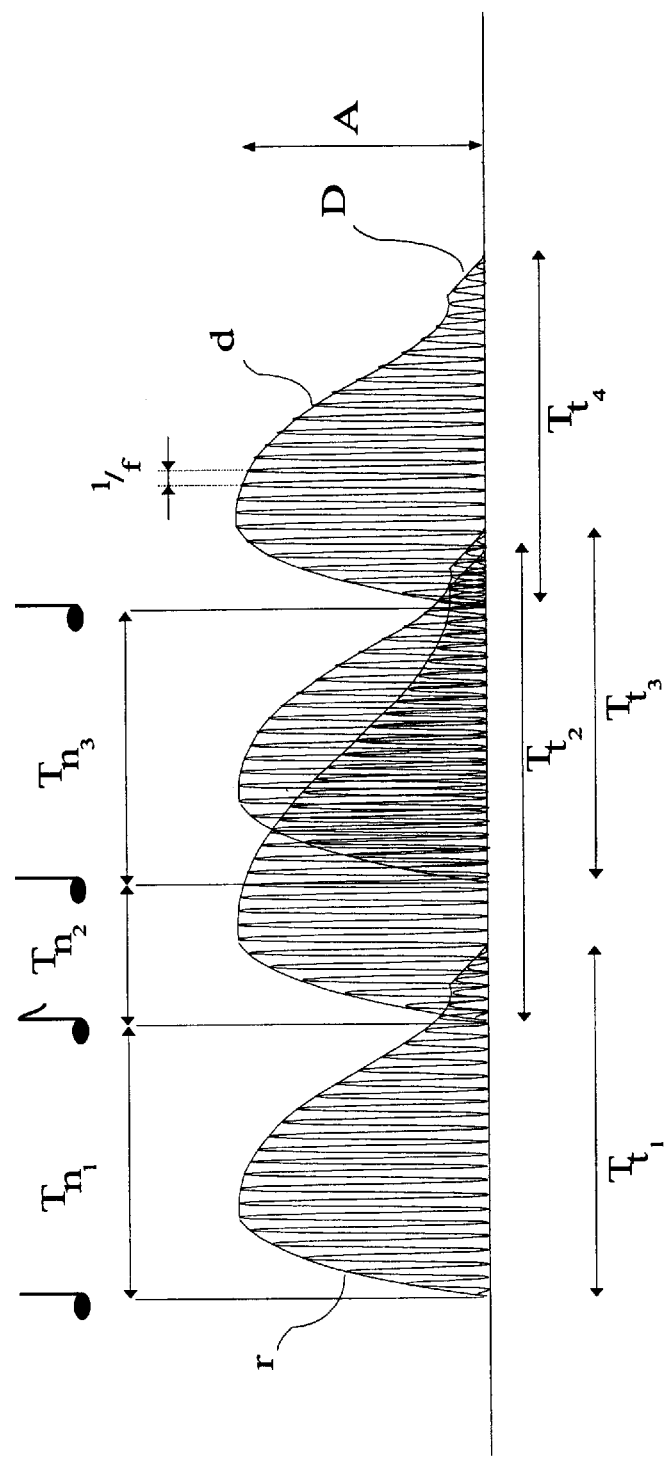
FIG. 7 shows a very simple sequence of sounds from the music synthesizer and illustrates the generator parameters.

In FIG. 7 these parameters for generation of voice and tempo is illustrated. FIG. 7 is a plot of the signal energy of a part of a music signal. It is illustrated that a tone (sine-wave with harmonic distortion, fundamental frequency f and amplitude A) is generated with fade-in and fade-out time-constants $t_r$ and $t_d$ determined by the $k_3$ coefficient. Furthermore, it is shown (exaggerated since the truncation takes the form of an exponential decay multiplied with a linear decay) that the envelope and thus the duration of the tone is truncated (the slope D) by the multiplier 162 which is controlled by the $k_1$ coefficient. Further, it is shown that the time $T_N$ between tone starts can be shorter than the duration of the tone $T_t$ and that tone start times may be varied $T_{N1}$, $T_{N2}$ . . . . The linear decay is controlled by the block 162, in the form of a multiplication with a factor which is initialized to 1 and subsequently reduced by an amount $k_1$ for every sample.

The tones of the various instruments may be played by any one of the set of sound generators 16a–16e. Thus, it is not necessary to provide different types of sound generators for different instruments.

What is claimed is:

1. An ear level electronic device comprising a housing that is adapted to be worn behind the ear, in the ear, or in the ear canal, and to enclose a music synthesizer for generation of a first electrical signal representing music and an output transducer for conversion of the first electrical signal into sound wherein the music synthesizer comprises a set of sound generators and a controller (6) for controlling the set of sound generators (16a–16e) and comprising at least a first pseudo-random number generator, and wherein control parameters of the set of sound generators (16a–16e) are calculated from numbers generated by the first pseudo-random number generator.

2. An electronic device according to claim 1, comprised in a digital hearing aid having the housing, an input transducer (1) for transforming an acoustic input signal into a second electrical signal, a digital signal processing means (2) for compensating a hearing deficiency by generation of a third electrical signal based on the second electrical signal, and wherein the output transducer (3) converts a combination of the first and third signals into sound.

3. An electronic device according to claim 1, comprised in a digital hearing aid having the housing, an input transducer (1) for transforming an acoustic input signal into a second electrical signal, a digital signal processing means (2) for compensating a hearing deficiency by generation of a third electrical signal based on a combination of the first and the second electrical signals, and wherein the output transducer (3) converts the third electrical signal into sound.

4. An electronic device according to claim 1, for use in treatment of tinnitus.

5. An electronic device according to claim 4, wherein the music synthesizer is adapted to present the synthesized music at the output transducer (3) with a loudness level that does not mask the tinnitus completely.

6. An electronic device according to claim 1, wherein the control parameters of the set of sound generators (16a–16e) comprises a tone frequency control parameter.

7. An electronic device according to claim 6, wherein the control parameters of the set of sound generators (16a–16e) comprises a tone fade-in parameter.

8. An electronic device according to claim 6, wherein the control parameters of the set of sound generators (16a–16e) comprises a tone fade-out parameter.

9. An electronic device according to claim 6, wherein the control parameters of the set of sound generators (16a–16e) comprises at least one harmonic control parameter.

10. An electronic device according to claim 6, wherein the control parameters of the set of sound generators (16a–16e) comprises a tone amplitude parameter.

11. An electronic device according to claim 6, further comprising a second pseudo-random generator, and wherein a second subset of control parameters of the control parameters of the set of sound generators (16a–16e) are calculated from numbers generated by the second pseudo-random number generator while a different first subset of control parameters of the control parameters of the set of sound generators (16a–16e) are calculated from numbers generated by the first pseudo-random number generator.

12. An electronic device according to claim 6, further comprising a temporal generator comprising a third pseudo-random generator, and wherein time periods between start of tone generation are determined by numbers generated by the third random generator.

13. An electronic device according to claim 6, wherein one of the set of sound generators is controlled by an independent set of three pseudo-random generators.

14. An electronic device according to claim 6, further comprising a fourth pseudo-random generator for controlling the number of active sound generators.

15. An electronic device according to claim 14, wherein one pseudo-random number generator is adapted to generate a sequence of self-similar numbers.

16. An electronic device according to claim 14, wherein one pseudo-random number generator is adapted to generate a sequence of fractal numbers.

17. An electronic device according to claim 15, wherein the controller 6 further comprises a selector unit 15 for the selection of an idle sound generator from the set of sound generators 16a–16e for generation of a tone.

18. An electronic device according to claim 17, wherein at least one of the set of sound generators (16a–16e) comprises a second order IIR filter for generation of an exponentially decaying sine shaped signal upon reception of an input impulse.

19. An electronic device according to claim 18, wherein the at least one sound generator further comprises a multiplier (162) with a linear decaying factor causing the generated signal amplitude to reach zero within a finite time period.

20. An electronic device according to claim 19, wherein the at least one sound generator further comprises a distortion circuit (163) for adding harmonics to the generated sine shaped signal.

21. A binaural hearing aid system comprising a first electronic device according to claim 1 to be positioned in one ear of a user, and a second electronic device according to claim 1 to be positioned in the other ear of the user.

22. A binaural hearing aid system comprising a first electronic device to be positioned in one ear of a user, and a second electronic device to be positioned in the other ear of the user, each of said first and second electronic devices comprising a housing that is adapted to be worn behind the ear, in the ear, or in the ear canal, and to enclose a music synthesizer for generation of a first electrical signal representing music and an output transducer for conversion of the first electrical signal into sound, wherein the first electronic device synthesizes music that is different from music synthesized by the second electronic device.

23. A tinnitus treatment method comprising the steps of synthesizing music with a music synthesizer for automatic generation of electronic signals representing music, converting the signals into sound, and directing the sound towards an ear of a person suffering from tinnitus, further comprising the step of sequentially generating a first pseudo-random number, and wherein the electronic signals are derived from the generated pseudo-random number.

24. A method according to claim 23, further comprising the step of compensating for another hearing deficiency of the person.

25. A method according to claim 23, further comprising the step of adjusting the sound loudness to a loudness level that do not to mask the tinnitus completely.

26. A method according to claim 23, further comprising the step of generating a tone based on the generated pseudo-random number.

27. A method according to claim 26, further comprising the step of generating the signal with a fade-in time constant based on the generated pseudo-random number.

28. A method according to claim 26, further comprising the step of generating the signal with a fade-out time constant based on the generated pseudo-random number.

29. A method according to claim 26, further comprising the step of generating the signal with a harmonic distortion based on the generated pseudo-random number.

30. A method according to claim 26, further comprising the step of generating the signal with an amplitude based on the generated pseudo-random number.

31. A method according to claim 26, further comprising the steps of sequentially generating a second pseudo-random number, and synthesizing the signal with a parameter based on the first pseudo-random number and another parameter based on the second pseudo-random number.

32. A method according to claim 26, further comprising the steps of sequentially generating a third pseudo-random number, and synthesizing the signal with a time period between start of tone generation determined by numbers generated by the third random generator.

33. A method according to claim 26, wherein one pseudo-random number generator is adapted to generate a sequence of self-similar numbers.

34. A method according to claim 26, wherein one pseudo-random number generator is adapted to generate a sequence of fractal numbers.

35. A method according to claim 26, wherein music is synthesized and directed towards one ear of a user, and different music is synthesized and directed towards the other ear of the user.

36. A tinnitus treatment method comprising the steps of generating a random number with a pseudo-random number generator, calculating parameters of a tone from the generated random number, operating a sound generator for generating the tone according to the calculated parameters, and directing the sound towards an ear of a person suffering from tinnitus.

37. The method according to claim 36, comprising the step of transforming an acoustic input signal into a second electrical signal, generating in a digital signal processing means a third electrical signal based on the second electrical signal and adapted for compensating for a hearing deficiency of the person, combining the first and third electrical signals into a fourth electric signal, and converting in an output transducer the fourth electric signal into sound.

* * * * *

UNITED STATES PATENT AND TRADEMARK OFFICE
CERTIFICATE OF CORRECTION

PATENT NO. : 6,816,599 B2
DATED : November 9, 2004
INVENTOR(S) : Thilo Volker Thiede and Carl Ludvigsen It is certified that error appears in the above-identified patent and that said Letters Patent is hereby corrected as shown below:

<u>Title page,</u>
Item [73], Assignee, delete "Topholm & Westermann APS" and insert
-- Widex A/S --.

Signed and Sealed this

Fifteenth Day of November, 2005

JON W. DUDAS
*Director of the United States Patent and Trademark Office*